United States Patent
Farquharson et al.

(10) Patent No.: US 7,462,492 B2
(45) Date of Patent: *Dec. 9, 2008

(54) APPARATUS FOR EFFECTING CHEMICAL SEPARATION AND PLURAL-POINT SERS DETECTION USING METAL-DOPED SOL-GELS

(75) Inventors: Stuart Farquharson, Meriden, CT (US); Paul Maksymiuk, South Windsor, CT (US)

(73) Assignee: Real-Time Analyzers, Inc., Middletown, CT (US)

(*) Notice: Subject to any disclaimer, the term of this patent is extended or adjusted under 35 U.S.C. 154(b) by 724 days.

This patent is subject to a terminal disclaimer.

(21) Appl. No.: 11/193,894

(22) Filed: Jul. 29, 2005

(65) Prior Publication Data

US 2005/0282287 A1 Dec. 22, 2005

Related U.S. Application Data

(62) Division of application No. 10/372,622, filed on Feb. 21, 2003, now Pat. No. 6,943,032.

(51) Int. Cl.
*G01N 21/76* (2006.01)

(52) U.S. Cl. .................................. 436/172; 436/164

(58) Field of Classification Search .................. None
See application file for complete search history.

(56) References Cited

U.S. PATENT DOCUMENTS

| 5,308,495 A | 5/1994 | Avnir et al. |
| 5,693,152 A | 12/1997 | Carron |

FOREIGN PATENT DOCUMENTS

| EP | 0133189 | 10/2001 |

OTHER PUBLICATIONS

On-Column Surface-Enhanced Ramon Spectroscopy Detection in Capillary Electrophoresis Using Running Buffers Containing Silve Colloidal Sollutions William F. Nirode, Gerald L. Devault and Michael J. Sepaniak (Anal. Chem. 2000, 72, 1866-1872); see especially p. 1867 col. 2, line 9 and Figures 3 and 4.

(Continued)

*Primary Examiner*—Yelena G Gakh
(74) *Attorney, Agent, or Firm*—Ira S. Dorman

(57) ABSTRACT

Sol-gel beds and deposits are utilized for SERS analysis of liquid analytes. Measurements are made at multiple points along the length of a column or channel to increase, very significantly, the speed of analysis, and use of the same medium to both separate the chemicals and also for SERS greatly reduces the complexity of such apparatus and enhances the efficiency of the method.

8 Claims, 2 Drawing Sheets

OTHER PUBLICATIONS

Molecular-Specific Chromatographic Detector Using Modified SERS Substrates, Keith T. Carron and Brian Kennedy (Anal. Chem. 1995, 67, 3353-3356); see especially Figures 1 and 3.

Determination of Purine Bases by Reversed-Phase High-Performance Liquid Chromatography Using Real-Time Surface-Enhanced Raman Spectroscopy, Rongsheng, Fan Ni, and Therese M. Cotton (Anal. Chem. 1991, 63, 437-442); see especially Figures 1 and 6.

Direct Analysis of High-Performance Think Layer—Chromatography Spots of Nucleic Purine Derivatives by Surface-Enhanced Raman Scattering Spectrometry, Shuichi Kawasaki, Tataro Imasuka, and Nobuhiko Ishibashi (Anal. Chem. 1987, 59, 525-527).

Fast Spatially Resolved Surface-Enhanced Raman Spectrometry on a Silver Coated Filter Paper Using Change-Coupled Device Detection By: Cabalin et al., Anal. Chem. Acta, 1995, v. 310, pp. 337-345.

Silver Coated Capillary Tube for Surface-Enhanced Raman Scattering, by Li et al., Vibrational Spectr., 1992 v. 3, pp. 115-120.

APPARATUS FOR EFFECTING CHEMICAL SEPARATION AND PLURAL-POINT SERS DETECTION USING METAL-DOPED SOL-GELS

CROSS REFERENCE TO RELATED APPLICATION

This application is a divisional of U.S. patent application Ser. No. 10/372,622, filed Feb. 21, 2003 and now issued as U.S. Pat. No. 6,943,032, the entire specification of which is hereby incorporated hereinto by reference thereto.

STATEMENT REGARDING FEDERALLY SPONSORED RESEARCH OR DEVELOPMENT

The United States Government has rights in this invention pursuant to National Science Foundation Contract No. DMI-0060258.

BACKGROUND OF THE INVENTION

The combination of chemical separation and analysis has long been recognized as invaluable to the analytical chemist in identifying chemicals at extremely low concentrations in complex matrices. For example, a drug and its metabolites can be effectively separated from blood plasma, using gas chromatography, and thereafter identified by the chemical fragments detected by mass spectrometry (see J. Chamberlain, The Analysis of Drugs in Biological Fluids, CRC Press, Boca Raton, 995, 2nd ed. chap. 6 and 7).

More recently, the combination of liquid chromatography, or flow injection analysis, with surface-enhanced Raman spectroscopy (SERS) has been investigated for such applications (see J-M. L. Sequaris and E. Koglin, Anal. Chem., 59,525 (1987); R. D. Freeman, R. M. Hanmaker, C. E. Meloan, and W. G. Fateley, Appl. Spectrosc., 42,456-460 (1988); F. Ni, R. Sheng and T. M. Cotton, Anal. Chem., 62, 1958(1990); G. T. Taylor, S. K. Shanna and K. Mohanan, Appl. Spectrosc., 44,635 (1990); R. Sheng, F. Ni and T. M. Cotton, Anal. Chem., 63,437 (1991); N. J. Pothier and R. K. Force. Appl. Spectrosc., 46, 147 (1992); L. M. Cabalin, A. Ruperez and J. J. Laserna, Talanta, 40, 1741 (1993); K. T. Carron and B. J. Kennedy, Anal. Chem., 67. 3353 (1995); L. M. Cabalin, A. Ruperez and J. J. Laserna, Anal. Chim. Acta, 318, 203(1996); N. J. Szabo and I. D. Winefordner, Appl. Spectrosc., 51.965 (1997); B. J. Kennedy, R. Milofsky and K. T. Carron, Anal. Chem., 69, 4708 (1997); and W. F. Nirode, G. L. Devault, M. J. Sepaniak and R. O. Cole, Anal. Chem., 72, 1866(2000)). Advantages of this combination of techniques include minimal sample preparation requirements, unrestricted use of water in the mobile phase, high chemical specificity through abundant molecular vibrational information, and extreme sensitivity, as demonstrated by the detection of single molecules. (See K. Kneipp, Y. Wang, R. R. Dasari and M. S. Feld, Appl. Spectrosc., 49,780(1995); and S. Nie and S. R. Emory, Science, 275, 1102 (1997)).

Previous research has employed primarily the three most common methods of generating SERS; i.e., using roughened silver or gold electrodes, using silver or gold-coated substrates, and using silver or gold colloids for detecting separated analytes. The lattermost method has gained the greatest amount of attention, since colloids can be prepared easily and inexpensively, and mixing of the colloids with the chromatographic column effluent, using flow injection, is reproducible. Care must be taken however to control aggregation of the colloids so that the amount of Raman signal enhancement is maintained. Also, a range of experimental variables, such as analyte concentration and pH, can strongly influence aggregation and, to some extent, limit applications; the choice of mobile phase is similarly limited by the need to maintain colloid integrity.

Recently, as described by Farquharson et al. in copending and commonly owned U.S. application Ser. No. 09/704,818 (published as International Publication No. WO 01/33189 A2, dated 10 May 2001), the entire specification of which is hereby incorporated by reference thereto, sol-gels have been developed to trap silver or gold particles as an improved method of generating plasmons for SERS (see also S. Farquharson, P. Maksymiuk, K. Ong and S. D. Christesen, SPIE, 4577, 166(2002); F. Akbarian, B. S. Dunn and J. I. Zink, J. Chem. Phys., 99, 3892 (1995); T. Murphy, H. Schmidt and H. D. Kronfeldt. SP1E, 3105, 40 (1997); and Y. Lee, S. Dai and J. Young, J. Raman Spectrosc. 28, 635 (1997)). It is appreciated that, once the sol-gel has formed, the particle size and aggregation of the metal dopant are stabilized, albeit changes in pH may still result in variable Raman signal intensities, such as in the case of weak acids and bases, where the relative concentrations of the ionized and unionized forms may be influenced. Also, it has been shown that many of the common solvents, such as acetone, methanol, and water, can be used equally with these metal-doped sol-gels in generating SERS of analytes.

In accordance with other recent developments, moreover, sol-gels have been used as the stationary phase in columns for liquid- and gas-phase chromatography, affording advantages in both the preparation of columns and also in their performance. The sol-gel approach enables deactivation, coating, and immobilization to be combined as a single step, while the sol-gels have shown reduced tailing, improved separation, and broader application to solvents and analytes.

Microchip devices have also been employed for effecting chemical separations (see Jacobson, S. C., Hergenröder, R., Koutny, L. B., & Ramsey, J. M. "High-Speed Separations on a Microchip," Anal. Chem., 66, 1114-1118 (1994); Jacobson, S. C., Hergenröder, R., Koutny, L. B., Warmack, R. J., & Ramsey, J. M. "Effects of Injection Schemes and Column Geometry on the Performance of Microchip Electrophoreis Devices," Anal. Chem., 66, 1107-1113 (1994); Jacobson, S. C. Hergenröder, R., Koutny, L. B. & Ramsey, J. M. "Open Channel Electro-chromatography on a Microchip," Anal. Chem., 66, 2369-2373 (1994); and Moore, Jr., A. W., Jacobson, S. C. & Ramsey, J. M. "Microchip Separations of Neutral Species via Micellar Electrokinetic Capillary Chromatography," Anal. Chem., 67, 4184-4189 (1995)).

SUMMARY OF THE INVENTION

It is the broad object of the present invention to provide a novel method and apparatus for the separation and immediate qualitative and quantitative analysis of components of liquid samples.

A more specific object of the invention is to provide such a method and apparatus by which separation and analysis can be effected at a high rate of speed.

It has now been found that certain of the foregoing and related objects of the invention are attained by the provision of a method for substantially simultaneously separating and detecting at least one analyte compound, wherein a sample solution containing a plurality of compounds, including at least one analyte compound, is transported through or along a metal-doped, surface-enhanced Raman-active sol-gel medium in sufficiently intimate chemical and/or physical contact for effecting separation of the "at least one" analyte compound. Substantially concurrently, the medium is irradiated with excitation radiation to generate inelastically scattered Raman radiation, at least a portion of which is collected and analyzed to determine the presence of the analyte compound in the sample solution. The sol-gel medium will usually comprise or define an elongate path for the sample solution (such as in a capillary column or a microchip channel), and the Raman radiation is collected at a plurality of locations along the length of the elongate path, for use in the analysis.

Other objects of the invention are attained by the provision of apparatus for effecting, substantially simultaneously, separation of at least one analyte compound from a sample solution containing a plurality of dissolved compounds, and detection of the "at least one" analyte compound. The apparatus comprises elongate containment means for containing a porous medium and having an entrance for introducing a sample solution thereinto, and a quantity of at least one metal-doped, surface-enhanced Raman-active sol-gel contained in the containment means and providing such a porous medium. The containment means is sufficiently transparent to excitation radiation, at least at a plurality of locations spaced from the entrance along its length, to permit transmission of excitation radiation effective for generating measurable amounts of inelastically scattered Raman radiation, and it is sufficiently transparent to such scattered radiation, at least at the same plurality of locations, to permit transmission of measurable amounts thereof. The porous medium defines a flow path through the containment means along at least the "plurality of locations," and is of such character as to promote intimate physical and/or chemical contact with a sample solution transported along the defined flow path.

The apparatus of the invention may desirably include a microchip card substrate, with the elongate containment means comprising a microchannel in the substrate or a capillary tube on the substrate, and with the substrate having a plurality of ports communicating with the channel and providing entrance-defining and exit-defining means. The porous medium will, in such embodiments, advantageously comprise a lining deposited on a wall of the channel or tube, or a packed bed in the channel or tube, defining the sample flow path.

The present invention uniquely combines two functions of sol-gels; i.e., (1) the ability to separate chemicals, and (2) the ability to immobilize metal particles that promote SER scattered radiation from chemicals in solution, which in turn enables analyses to be performed in a highly effective and efficient manner. One or more suitable optical probes, capable of excitation and collection of Raman photons, scan the length of a suitably transparent column, or monitor it at a plurality of discrete locations, for the detection of separated chemical species, thereby enabling a complete analysis to be accomplished in five minutes or less. The rate of the chemical and physical contact that is necessary for effecting separation of the species can be promoted by driving the analyte solution through or along a sol-gel bed or deposit under applied positive or negative pressure.

DETAILED DESCRIPTION OF THE PREFERRED AND ILLUSTRATED EMBODIMENTS

The silver-doped SER-active sol-gels employed in the examples that follow were prepared in accordance with the method of Lee and Farquharson (SPIE 4206, 140 (2001). In essence, a silver amine complex, consisting of a 5:1 v/v solution of 1 N $AgNO_3$ and 28% $NH_3OH$, is mixed with an alkoxide, consisting of a 2:1 v/v solution of methanol and tetramethyl orthosilicate (TMOS) in a 1:8 v/v silver amine: alkoxide ratio.

As an example of a fabrication technique that can be used in the practice of the invention, a 0.15 mL aliquot of the foregoing mixture is transferred to a 2 mL glass vial, which is spun to coat its inside walls. After sol-gel formation, the incorporated silver ions are reduced with dilute sodium borohydride, followed by a water wash to remove residual reducing agent. The sol-gel coating is scraped from the walls of the vial, and is converted to a homogeneous powder by grinding with a mortar and pestle.

Figure 1:
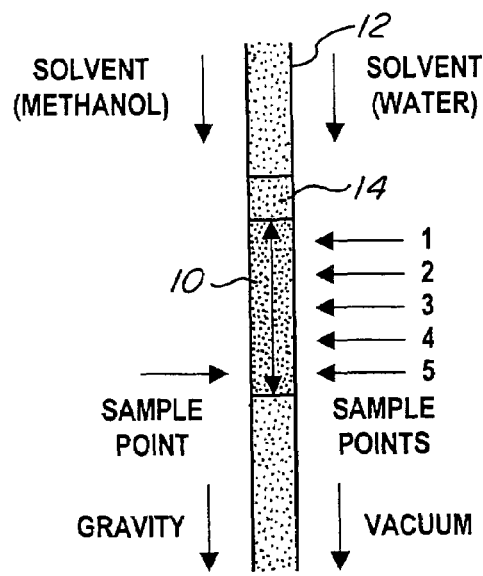
FIG. 1 is a diagrammatic representation of a packed bed column used for separation and analysis of dissolved analytes, showing both the traditional, gravity-flow (with inherent capillary action) method of solution transport, with a single sampling point, and also a vacuum-assisted transport method with, in accordance with the present invention, multiple sampling points.

As depicted in FIG. 1, the ground sol-gel 10 is packed into a 5 mm segment of a 4 cm length of a 1.0 mm diameter melting point capillary tube 12, using a sterile cotton plug 14 to hold the powder in place, and the top is fit with a 1.0 mL disposable plastic pipette (not shown) to allow delivery of 10 μL samples to the rudimentary liquid chromatography column so prepared. A diaphragm pump (also not shown) is attached to the exit end of the column to enable vacuum-assisted transport of the test solution through the sol-gel bed.

The column is fixed vertically at the focal point of a microscope objective (20×0.4) attached to an XYZ positioning stage, to focus the beam into the sample and to collect radiation scattered back along the axis of incidence. A notch filter is provided to reflect the excitation laser beam to the microscope objective, and to pass the collected Raman-scattered radiation.

Two 3 m lengths of fiber optic were used to deliver the laser energy (200 micron diameter) and to collect the Raman radiation (365 micron diameter). A Nd:YAG laser provided 50 mW of 1064 nm excitation radiation at the sample, and a Fourier transform Raman spectrometer, equipped with an InGaAs detector, was used for spectra acquisition.

EXAMPLE ONE

Insofar as the flow of analyte solution is concerned, the following experiment (depicted along the left side of FIG. 1) mimics traditional liquid chromatography. A solution of $8 \times 10^{-3}$M p-aminobenzoic acid and $4 \times 10^{-3}$M phenyl acetylene was prepared in methanol to demonstrate separation of polar and non-polar chemicals. A 10 μl quantity of the solution was added to the top of a separation and analysis column, constituted and assembled as hereinabove described. A 1 mL quantity of methanol was added as a carrier solvent, and allowed to elute under the forces of gravity and capillary action only. Using an optical probe coupled to a Raman spectrometer, which measured the surface-enhanced Raman spectra at the bottom of the column as a function of time, it was confirmed that the methanol solvent caries the non-polar PA through the column ahead of the polar PABA.

Figure 2:
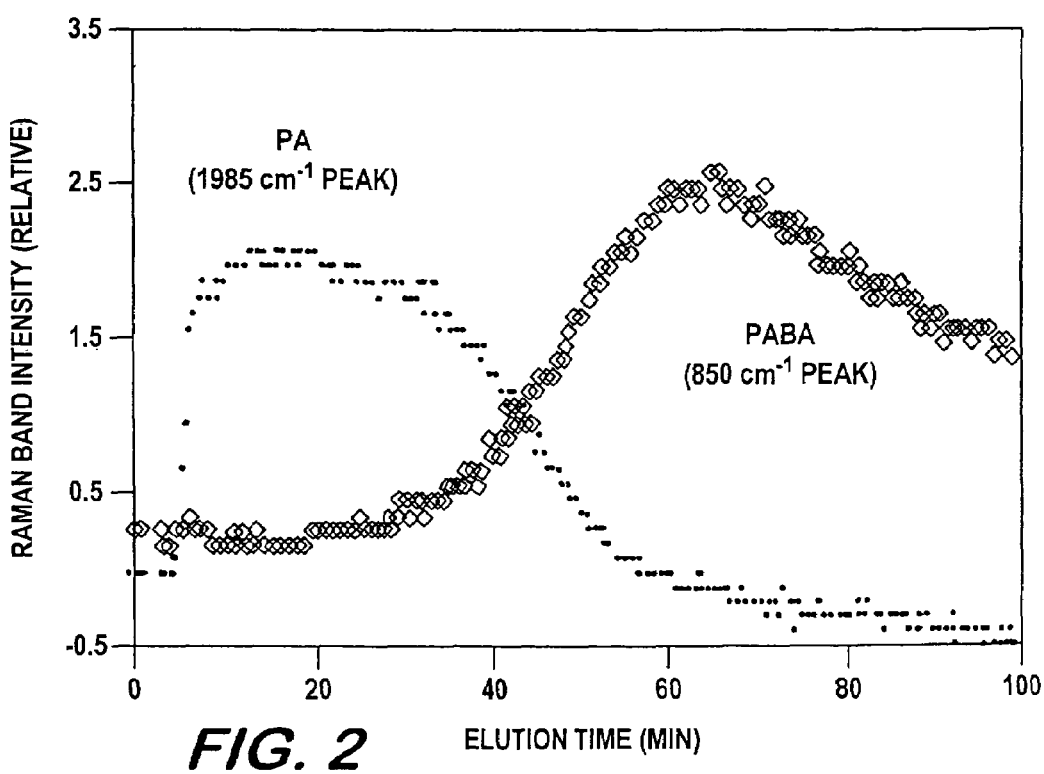
FIG. 2 is a plot of Raman band relative intensity over a period of 100 minutes, constituting an elution profile of phenyl acetylene (PA) and p-amino-benzoic acid (PABA)

More specifically the microscope objective was positioned 0.5 mm from the bottom edge of the 5 mm length of packed sol-gel, and scans were made and averaged every 30 seconds to produce spectra. Unique bands for PA and PABA, at 1985 $cm^{-1}$ and 850 $cm^{-1}$, respectively, were used to plot relative concentration as a function of time. FIG. 2 shows the elution profiles generated for both analytes during a 100 minute test period, which verify that chemical separation does occur. These data also show however that, in the absence of any external driving force, a significant period of time is required.

EXAMPLE TWO

This example demonstrates that techniques can be applied for driving the solution through the column to substantially reduce analysis time. Thus, a second experiment (depicted along the right side of FIG. 1) employs an identical sample but uses a 50/50 v/v mixture of methanol and water as the carrier solvent, rather than methanol alone. In addition, a vacuum of a 50 cm of Hg was applied for 30 seconds to draw the sample through the column. Due to the addition of water in the solvent, the separation is reversed because, in the present case, the alkoxide, TMOS, used to prepare the sol-gel is hydrophilic (i.e., water carries the polar PABA through the column first), demonstrating flexibility of the concept.

Since the entire length of the column is SER-active, moreover, the extent of separation could be and was, in accordance with the instant invention, measured by moving the microscope objective to five different positions along its length, enabling the collection of spectra at each level. More specifically, spectra, plotted in FIG. 3, were collected at five discrete points spaced 1-mm apart, the first being located at a level 0.5 mm from the top edge of the sol-gel bed, with each spectrum consisting of scans averaged for 30 seconds. Spectra (1) and (5), obtained at the top and bottom of the column, indicate pure PA and PABA, respectively; the intermediate spectra represent mixtures of the two analytes.

Because there was no need to wait for the analytes to elute past a single measurement point at the end of the column (i.e., the separated chemicals can be measured wherever they occur along the column, since it is SER-active along its entire length), each analyte could be identified quickly; complete analysis was performed in three minutes, as compared to at least 80 minutes in the traditional method. The time savings realized provides many significant benefits, particularly for trace chemical analyses of multi-component systems.

Figure 3:
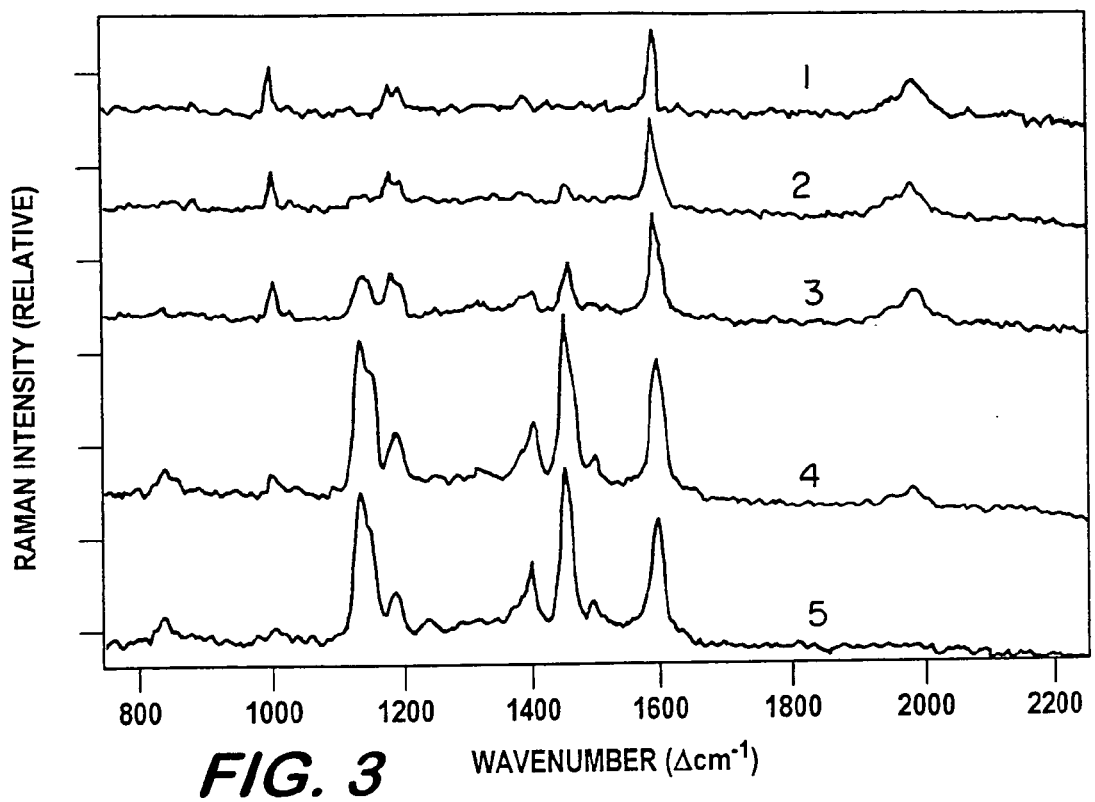
FIG. 3 presents a series of spectra, taken at five points along the length of a sol-gel packed column used for separation and measurement of concentrations of PA and PABA.

The series of spectra presented in FIG. 3 also demonstrates the power of Raman spectroscopy, in that each chemical can be easily identified, either isolated or as a mixture. Although previous knowledge of, or expectation as to, the sample composition simplifies the task, spectral matching and deconvolution software programs, or like techniques, can be used to handle unknown components.

EXAMPLE THREE

Figure 4:
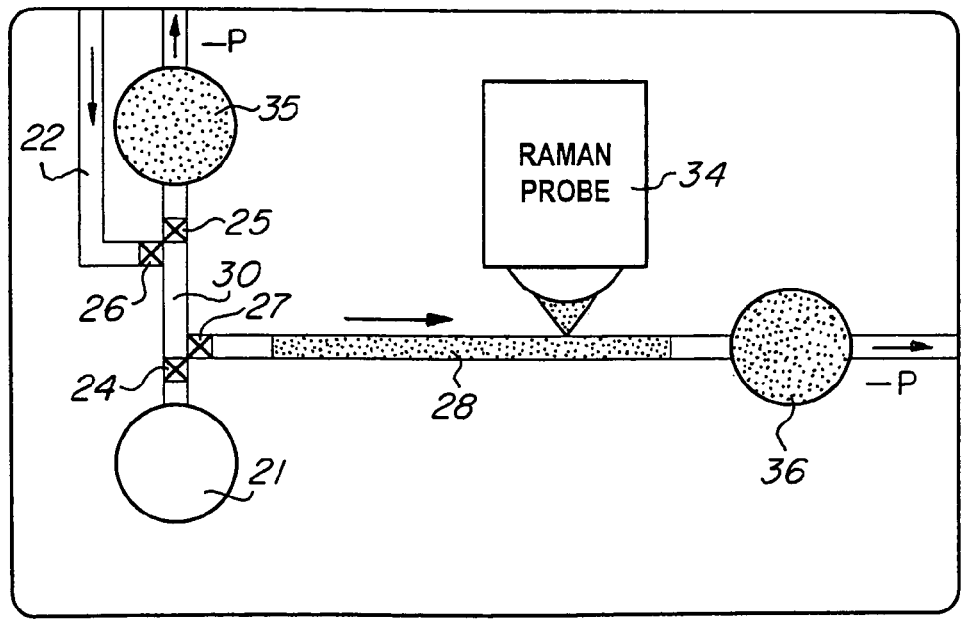
FIG. 4 is a diagrammatic representation of a microchip device incorporating a SER-active sol-gel chemical separation channel and enabled by the present invention.

A microchip chemical analyzer, diagrammatically illustrated in FIG. 4, constitutes a form of apparatus enabled by the present invention. The analyzer comprises a card, generally designated by the numeral 20, which contains a sample input port 21, a solvent entry channel 22, valves 24, 25, 26 and 27, and a SER-active sol-gel microchannel 28. In this instance the sol-gel takes the form of a porous lining deposited on the wall of the channel 28 (albeit a packed channel is also feasible), and an applied vacuum driving force promotes rapid passage through the channel 28 coupled with the physical and chemical contact required for effective separation.

In use, a sample (e.g., a drop of blood) is applied to a porous cover, such as a membrane or sponge overlying the sample entry port 21 (or the port may be of septum-like form), typically using an eye dropper, a pipette, or a syringe. The sample is then urged, such as by vacuum applied at the waste chamber 35 (or alternatively, by positive pressure such as may be applied by a pipette or syringe, always using of course appropriate connections), into a load channel section 30, for which purpose the valves 24 and 25 would be opened and the valves 26 and 27 would be closed. Then, with valves 24 and 25 closed to isolate the sample entry port 21 and the waste chamber 35, and the valves 26 and 27 opened, solvent is drawn (or alternatively, pushed) through the channel 22 to drive the loaded sample through the passage of the channel 28 to waste chamber 36, again with vacuum (or pressure) applied thereat. Chemical components of the sample interact with the sol-gel deposit and are thereby separated, allowing identification and quantitation of the target analyte(s) by SER spectroscopy using a Raman optical probe such as a suitably mounted objective 34 with appropriate interface optics. The microchip card 20 would typically fit onto a platform that aligns interconnects for the sample/solvent delivery and flow-control system, and that dynamically positions the Raman probe objective to enable spectral analyses to be effected along the length of the SERS-active portion of the channel 28, as described.

It will be appreciated that virtually any sol-gel, in powdered, particulate or other finely divided form, or in the form of a porous, passage-defining deposit, can be used as a separation/analysis medium in the practice of the present invention. Selectivity may be afforded by the inherent electropotential of the metal dopant (electronegative or electropositive), by the hydrophobic or hydrophilic nature of the sol-gel medium, etc. Thus, while the examples set forth above employ a silver-doped sol-gel, doping with gold is regarded to be equally important; copper, and less desirably nickel, palladium, and platinum, and alloys and mixtures thereof, can of course be utilized as well.

The nature and structure of the containment "vessel" can vary widely, and is not limited to columns; as described above, for example, the analysis apparatus may comprise glass or plastic microchannels incorporated into microchip analyzers. Albeit the sample path will usually be rectilinear, it will be appreciated that the elongate path referred to herein may be curvilinear and of relatively complex, compound configuration as well. A fluidic device used to add solvent and push and/or pull the sample through the SER-active medium, for effecting sample introduction and separation, can take many different forms, it being appreciated that the functional features of the device may be important from the standpoint of assuring the intimacy of contact necessary for efficient separation of the analyte compound(s). Similarly, the Raman probe can take many different forms, as will be apparent to those skilled in the art; as one example, however, the probe may desirably comprise six collection optical fibers surrounding one excitation fiber.

Numerous applications can benefit from the method and apparatus of the invention, including, for example, the detection of contaminants in groundwater (e.g. $CN^-$, $CrO_4^-$), the determination of drug presence and efficacy, by analysis for a parent constituent and/or its metabolites in a biological fluid, and the detection of chemical agent hydrolysis products in poisoned water; other applications will readily occur to those skilled in the art.

It should be understood that the term "solution" is used in a broad sense in the present description and claims. It is intended to encompass colloidal suspensions (of dispersed solid, semisolid, and liquid particles) in a fluid (gas or liquid) continuous phase, as well as true solutions (i.e., at the molecular or ionic level) of one or more dissolved substances in a simple or mixed fluid solvent.

Thus, it can be seen that the present invention provides a method and apparatus by which a metal-doped sol-gel can be used for the substantially simultaneous separation and SERS analysis of chemicals in solution. By measuring spectra at multiple points along a column or other elongate containment vessel or channel, with or without the application of a driving force to promote flow of the sample solution, moreover, contemporaneous quantitative and qualitative analyses of a solution of one or more analytes can be performed quickly and accurately.

Having thus described the invention, what is claimed is:

1. Apparatus for effecting separation of at least one analyte compound from a sample solution containing a plurality of dissolved compounds, and detection of the at least one analyte compound, comprising:

elongate containment means for containing a porous separation medium and being sufficiently transparent to excitation radiation, at least at one location, to permit transmission of excitation radiation effective for generating measurable amounts of surface enhanced Raman scattered radiation, and being sufficiently transparent to surface-enhanced Raman scattered radiation, at least at said one location along its length, to permit transmission of measurable amounts of such scattered radiation;

a quantity of at least one metal-doped, surface-enhanced Raman-active sol-gel contained in said containment means and providing a porous medium, said medium defining a flow path through said containment means past said at least one location, said medium being of such character as to promote intimate contact with a sample solution transported along said flow path; and means for defining an entrance for a sample solution to said flow path.

2. The apparatus of claim 1 wherein said elongate path is rectilinear.

3. The apparatus of claim 1 comprising a packed column of said Raman-active sol-gel.

4. The apparatus of claim 1 comprising a microchip card substrate bearing said elongate containment means.

5. The apparatus of claim 4 wherein said elongate containment means comprises a microchannel in said substrate, said substrate having a plurality of ports communicating with said microchannel and providing said entrance-defining means and an exit-defining means.

6. The apparatus of claim 1 wherein said porous medium comprises a lining deposited on a wall of said elongate containment means and defining said sample flow path.

7. The apparatus of claim 1 wherein the dopant metal of said sol-gel is silver, gold, copper, or an alloy or mixture comprised thereof.

8. Apparatus for effecting separation of at least one analyte compound from a sample solution containing a plurality of dissolved compounds, and detection of the at least one analyte compound, comprising:

elongate containment means for containing a porous medium and being sufficiently transparent to excitation radiation, at least at one location, to permit transmission of excitation radiation effective for generating measurable amounts of surface enhanced Raman scattered radiation, and being sufficiently transparent to surface-enhanced Raman scattered radiation, at least at said one location along its length, to permit transmission of measurable amounts of such scattered radiation;

a quantity of at least one metal-doped, surface-enhanced Raman-active sol-gel contained in said containment means and providing a porous medium, said medium defining a flow path through said containment means past said at least one location, said medium being of such character as to promote intimate contact with a sample solution transported along said flow path;

means for defining an entrance for a sample solution to said flow path; and means, operatively connected to said flow path, for applying a driving force to promote flow of a sample solution along said flow path.

* * * * *